United States Patent [19]

Dabrowski et al.

[11] Patent Number: 5,591,426
[45] Date of Patent: Jan. 7, 1997

[54] OPHTHALMIC SOLUTION FOR ARTIFICIAL TEARS

[75] Inventors: Henry P. Dabrowski, Naples; Anil Salpekar; O. William Lever, Jr., both of Pittsford, all of N.Y.

[73] Assignee: Bausch & Lomb Incorporated, Rochester, N.Y.

[21] Appl. No.: 380,931

[22] Filed: Jan. 31, 1995

Related U.S. Application Data

[63] Continuation of Ser. No. 86,421, Jul. 2, 1993, abandoned.

[51] Int. Cl.$^6$ .................. A61K 31/16; A61K 31/395
[52] U.S. Cl. .................. 424/78.04; 424/78.23; 424/78.36
[58] Field of Search .................. 424/78.04, 78.23, 424/78.36

[56] References Cited

U.S. PATENT DOCUMENTS

| | | | |
|---|---|---|---|
| 3,311,577 | 3/1967 | Rankin | 260/17 |
| 3,549,747 | 12/1970 | Krezanowski et al. | 424/78 |
| 3,856,919 | 12/1974 | Rankin | 424/78 |
| 3,920,810 | 11/1975 | Rankin | 424/80 |
| 3,947,573 | 3/1976 | Rankin | 424/80 |
| 3,987,163 | 10/1976 | Rankin | 424/78.04 |
| 4,013,576 | 3/1977 | Loshaek | 252/106 |
| 4,029,817 | 6/1977 | Blanco et al. | 424/329 |
| 4,039,662 | 8/1977 | Hecht et al. | 424/180 |
| 4,120,949 | 10/1978 | Bapatla et al. | 424/80 |
| 4,421,748 | 12/1983 | Trager et al. | 424/199 |
| 4,432,964 | 2/1984 | Shell et al. | 424/14 |
| 4,438,123 | 3/1984 | Smith | 424/270 |
| 4,470,965 | 9/1984 | Wolf et al. | 424/80 |
| 4,626,292 | 12/1986 | Sherman | 134/26 |
| 4,744,980 | 5/1988 | Holly | 514/915 |
| 5,061,714 | 10/1991 | Tadokoro et al. | 514/309 |
| 5,106,615 | 4/1992 | Dikstein | 424/78.04 |
| 5,141,665 | 8/1992 | Sherman | 252/106 |
| 5,264,449 | 11/1993 | Albaugh | 514/397 |

OTHER PUBLICATIONS

53 Fed. Reg. 7076 (Mar., 1988), 21 CFR Parts 349 and 369, Ophthalmic Drug Products for Over–the–Counter Human Use; Final Monograph; Final Rule.
Tiffany, Winter and Bliss, Current Eye Research, vol. 8, Nov. 5, 1989 "Tear Film Stability and Tear Surface Tension", pp. 507–515.

*Primary Examiner*—Jeffrey C. Mullis
*Attorney, Agent, or Firm*—Edward W. Black, Esq.

[57] ABSTRACT

An ophthalmic artificial tear solution is described for treating irritation and dryness of the eyes with a formulation that includes polyvinylpyrrolidone, a preservative such as benzalkonium chloride, glycerin and hydroxypropyl methylcellulose, wherein the composition is an aqueous solution having isotonic properties with respect to the eye. The ophthalmic solution of the invention is characterized as having a low viscosity, preferably less than 5 cps, and a low surface tension, preferably less than 40 dynes/cm, wherein wettability, retainability and comfort of the user are enhanced.

12 Claims, No Drawings

OPHTHALMIC SOLUTION FOR ARTIFICIAL TEARS

This application is a continuation application of copending application Ser. No. 08/086,421 filed on Jul. 2, 1993, now abandoned.

BACKGROUND OF THE INVENTION

The present invention relates to ophthalmic compositions that relieve eye irritation or dryness and provide lubrication for the eyes. More particularly, the invention relates to ophthalmic solutions that function as artificial tears and can be used, as needed, for temporary relief of and protection against eye irritation.

Many people suffer from temporary or chronic eye conditions wherein the eye's tear system fails to provide adequate tear volume or tear film stability to remove irritating environmental contaminants such as dust, pollen or the like. Where the tear film on ocular surfaces becomes discontinuous, the condition is often called "dry eye".

Such failures of the tear system result in significant personal discomfort, such as dry, itching, burning and irritating eyes. Treatment typically involves applying a slightly viscous solution in drop form to the eyes to provide at least a temporary wetting before the solution evaporates or is wiped away by operation of the eyelids. Since the solution tends to be cleared from the eye rather quickly, frequent dosing is generally necessary.

A key element of an artificial tears solution is a polymer system designed to mimic the action of mucin and or/lipids, which are the principal active natural components of tear fluid. The polymer system selected for artificial tears acts as a wetting agent in the eye and is responsible for contributing to tear film stability.

In addition to the active polymer system ingredients, a preservative system that is effective for maintaining solution sterility is typically necessary. Its purpose is to prevent bacteria and other organisms from contaminating the solution after its container has been opened and an initial dose has been used. Such a preservative is a necessary component of artificial tears where packaging is in other than single dose units.

An example of a prior artificial tears solution is described by Bapatla et al in U.S. Pat. No. 4,120,949. Bapatla pointed out that earlier commercially available artificial tear solutions had been either excessively viscous and, therefore, difficult to use or were so low in viscosity that the solution could not form a sufficiently long lasting film. Bapatla's artificial tear composition said to have a relatively long film life, contains polyvinyl alcohol (0.1–10.0%), hydroxyethyl cellulose (0.1–5.0%) and polyvinylpyrrolidone (0.1–20.0%). Bapatala's Examples report viscosities ranging between 5 and 270 cps. However, all but one are relatively high viscosities, in the 80–270 cps range. Surface tension of the solutions of the Examples ranged from between 33 and 45 dynes/cm.

In a review article on surface interfacial and molecular aspects of polymer bioadhesion of soft tissues, Nikolaos A. Pappas and Pierre A. Buri [Journal of Controlled Release, 2(1985) 257–275] quote A. J. Kinlock [J. Mater. Sci. 15 (1980) (2141] as stating that bioadhesion is enhanced for liquid adhesive materials characterized by zero or near zero contact angles and having relatively low viscosities. Tiffany et al, in "Tear Film Stability and Tear Surface Tension" Current Eye Research, Vol. 8, No. 5 (1989), finds a negative correlation between surface tension and break-up-time for tear film on the human eye. These works suggest that low surface tension may be a useful factor for artificial tears that must adhere readily to corneal surfaces.

A particularly useful wetting agent that does not unduly increase the viscosity of ophthalmic solutions is polyvinylpyrrolidone (PVP). PVP has a number of other characteristics that makes it useful in combination with the various well known components in ophthalmic solutions.

Rankin, in U.S. Pat. No. 3,920,810, notes that polyvinylpyrrolidone acts as a detoxicant, binding anti-toxins present in eye fluids and rendering them harmless. PVP also acts to protect a treatment solution by preventing its breakdown, through particle agglomeration. Additionally, PVP acts as a demulcent lubricant by means of a combination of adhesive and lubricating properties that aid in the spreading of the viscous solution.

Preferred preservatives utilized in ophthalmic solutions may include quaternary ammonium compounds, particularly benzalkonium chloride (BAK), as described by Hecht et al in U.S. Pat. No. 4,039,662. Although BAK is an effective preferred preservative, it is often limited in concentration and, hence, usefulness because of some users' sensitivity thereto.

Blanco et al, in U.S. Pat. No. 4,029,817, teaches that quaternary ammonium compounds, e.g. benzalkonium chloride, when combined with a detoxifying amount of certain polymers, may be utilized in contact lens cleaning solutions at BAK concentration levels otherwise known to be irritating and potentially harmful. A list of suitable polymers includes, among others, polyvinylpyrrolidone.

It would be desirable to provide a formulation that provides effective relief from dry and irritating eye conditions by means of components that combine to provide good wetting and retainability in the eye which formulation also includes a reliable preservative that is rendered substantially less irritating or non-irritating.

SUMMARY OF THE INVENTION

The present invention describes an eye drop formulation for relief from irritation or dryness of the eyes which eye drop provides lubrication and moisturizing for the eyes.

The present invention provides an ophthalmic aqueous solution that is useful as an artificial tear and comprises polyvinylpyrrolidone and an effective ophthalmic preservative, such as benzalkonium chloride, wherein the PVP provides adhesion of the composition to corneal surfaces, binds anti-toxins and complexes with BAK such that risk of irritation to the user is reduced.

The formulation of the invention is of low surface tension, preferably below 40 dynes/cm, and of low viscosity, preferably below 5 cps. Said composition further includes hydroxypropyl methylcellulose and glycerin to provide demulcent activity.

The composition may further include, as is well known, buffers, surface active agents and salts, such that the solution is substantially isotonic.

A preferred artificial tear composition of the invention, consists of:

(1) polyvinylpyrrolidone, preferably in an amount of about 0.1–1.5% by weight of said solution;

(2) benzalkonium chloride, preferably in an amount of about 0.01–0.10% by weight;

(3) hydroxypropyl methylcellulose, preferably in an amount of about 0.2–1.5% by weight of said solution; and (4) glycerin, preferably in an amount of about 0.2–1.0% by weight of said solution, wherein the composition is an aqueous solution having isotonic properties.

DETAILED DESCRIPTION OF THE INVENTION

The present invention is an ophthalmic solution that is principally characterized by low viscosity and low surface tension relative to previously known solutions. Preferably, at 25° C., the viscosity is less than about 5 cps and surface tension is less than about 40 dynes/cm. Both of these characteristics are useful in promoting good wettability and spread, as well as good retention and stability on the eye, without significant discomfort of the user.

In addition, the ophthalmic solution of the invention includes glycerin and hydroxypropyl methylcellulose which act as humectants. The humectants enhance water retention in the eye and enhance moisturizing capabilities of the solution. These identified materials also possess significant demulcent activity.

The key components of the formulation of the invention and preferred concentration thereof comprise:

| | |
|---|---|
| polyvinylpyrrolidone | 0.1–1.5% |
| benzalkonium chloride | 0.01–0.10% |
| hydroxypropyl methylcellulose | 0.2–1.5% |
| glycerin | 0.2–1.0% |

In addition, conventional and well known buffers, salts and the like may be included to form an isotonic, buffered system.

A key element of the ophthalmic artificial tear solution of the invention is the combination of polyvinylpyrrolidone and benzalkonium chloride. The PVP provides tear film stability and wetting of the corneal surfaces and also allows the use of BAK in effective preservative concentrations in the solution.

The polyvinylpyrrolidone (PVP) used in the compositions of the invention is a linear polymer of 1-vinyl-2-pyrrolidone groups, preferably having a molecular weight of about 35,000 to 51,000. Such materials are sold by ISP Technologies, Inc. under the trademark PLASDONE™ K-29/32. It is to be understood, however, that the invention is not limited to any specific PVP and that any equivalent PVP of pharmaceutical grade may be used.

The quaternary ammonium compound benzalkonium chloride is characterized as a mixture of alkyldimethyl benzylammonium chlorides. It is employed in a preferable concentration of about 0.01% by weight of the solution. The preserved formula is intended for use in the eye in the absence of a contact lens, since the use of benzalkonium chloride with contact lens is contraindicated due to irritation potential.

The solution of the invention is useful by contact lens wearers. Sorbic acid or other suitable ophthalmic preservatives that are not irritating to the eyes are used. Such a formula is also characterized by, at 25° C., very low viscosity (below 5 cps) and low surface tension (below 40 dynes/cm). Other suitable ophthalmic preservatives include chlorobutanol, disodium ethylenediamine tetra-acetate, polyquaternium-1, acetamide, alkyltrimethylammonium bromide, and cetyltrimethylammonium bromide. Another suitable surface active component is poloxamine.

The hydroxypropyl methylcellulose (HPMC) functions to provide a desired level of viscosity and to provide demulcent activity. It is characterized as a mixed ether of cellulose containing a variable proportion of methoxyl and 2-hydroxypropoxyl groups and is purchased from Dow Chemical under the trademark Methocel E 15 LV-Premium. It is to be understood that the invention is not limited to any specific hydroxypropyl methylcellulose and that any equivalent HPMC of pharmaceutical grade may be used.

The ophthalmic solutions of this invention preferably contain a buffer system to control pH. Any pharmaceutically acceptable buffer system may be utilized. A preferred buffer system is provided by sodium borate/boric acid in amounts necessary to produce a pH of about 6.0 to 8.0. A preferred pH range is about 6.5–7.8 and a most preferred range is about 7.1–7.5.

The ophthalmic solutions of this invention are isotonic with respect to the fluids of the human eye. These solutions are characterized by osmolalities of 270–330 mOsm/kg. Osmolality of the solution of the invention is adjusted by means of sodium chloride and potassium chloride.

The formulation of the invention may include a number of additional components to provide various effects, as is well known in this field. For example, the solution may include edetate disodium, which may function as a co-preservative and chelating agent.

The following examples illustrate the invention without limiting its scope. All percentages are by weight of the solution.

EXAMPLE 1

An aqueous solution of the invention is prepared, including the following ingredients:

TABLE

| | | |
|---|---|---|
| Polyvinylpyrrolidone | 1.00 mg/mL | 0.100% |
| Benzalkonium Chloride, 50% | 0.20 mg/mL | 0.020% |
| Hydroxypropylmethyl cellulose | 5.00 mg/mL | 0.500% |
| Glycerin | 2.00 mg/mL | 0.200% |
| Edetate Disodium | 0.30 mg/mL | 0.030% |
| Boric Acid | 3.00 mg/mL | 0.300% |
| Sodium Borate | 0.35 mg/mL | 0.035% |
| Potassium Chloride | 3.50 mg/mL | 0.350% |
| Sodium Chloride | 4.00 mg/mL | 0.400% |
| Purified Water | 1.00 mL | to 100% |

The formulation is prepared by adding each of NaCl, KCl Na Borate, Boric Acid, EDTA and HPMC (Type E15-LV Premium) to a volume of water that is 70–85% of the final batch volume, under agitation and initially heated to 80°–90° C. Each component is allowed to dissolve or disperse before adding the next. With continued agitation, the batch is cooled to 50° C. (±5° C.) and mixed for 20 minutes while cooling. Continuing to agitate, the PVP K-30, glycerin and BAK (50% solution) are each sequentially dissolved or dispersed. The batch is cooled under agitation to 20° C. (±5° C.) for a minimum of 20 minutes. The pH is then adjusted to 7.1–7.5 using increments of either 1N NaOH or 1N HCl. The solution is brought to final volume with 20°–30° C. water and mixed for at least 15 minutes. The BAK concentration is adjusted to a 95–110 ppm content.

EXAMPLE 2

Four samples of the formulation of Example 1 are prepared and characterized by viscosity and surface tension.

| Sample No. | Viscosity (cps at 25° C.) | Surface Tension (dynes/cm at 25° C.) |
|---|---|---|
| 1 | 2.1 | 35.2 |
| 2 | 2.1 | 33.8 |
| 3 | 2.1 | 33.4 |
| 4 | 2.1 | 33.1 |

What is claimed:

1. An ophthalmic solution useful as artificial tears consisting essentially of:

polyvinylpyrrolidone (PVP);

hydroxypropyl methylcellulose (HPMC);

Sodium borate/boric acid buffer:

glycerin; and an effective ophthalmic preservative, forming an aqueous solution having at 25° C., a viscosity of less than about 5 cps and a surface tension of less than about 40 dynes per centimeter.

2. The ophthalmic solution of claim 1 wherein said ophthalmic preservative is benzalkonium chloride (BAK), sorbic acid, chlorobutanol, disodium ethylenediamine tetraacetate, polyquaternium-1 or alkyltrimethylammonium bromide.

3. The ophthalmic solution of claim 2 wherein the preservative is benzalkonium chloride or cetyl trimethylammonium bromide.

4. The ophthalmic solution of claim 1 wherein

PVP is present at a level of about 0.1 to 1.5% by weight of said solution; and wherein said preservative is benzalkonium chloride at about 0.01–0.10% by weight of said solution.

5. The ophthalmic solution of claim 1 further including as components of said solution:

a surface active component; and a chelating component.

6. The ophthalmic solution of claim 5 wherein said chelating component is edetate disodium.

7. The ophthalmic solution of claim 5 wherein said surface active component is poloxamine or BAK.

8. An ophthalmic solution useful as an artificial tear, consisting essentially of:

polyvinylpyrrolidone in an amount of about 0.100%;

benzalkonium chloride in an amount of about 0.010% by weight;

sodium borate/boric acid buffer;

glycerin in an amount of about 0.200% by weight; and hydroxypropyl methylcellulose, in an amount of about 0.500% by weight of said solution;

wherein said composition is an aqueous solution, having isotonic properties with respect to an eye, a viscosity of about 1.5 to 5 cps and a surface tension of about 25 to 40 dynes/cm.

9. The composition of claim 8 further including effective amounts of sodium borate/boric acid buffer, edetate disodium as a chelating agent, and potassium chloride and sodium chloride as osmolality adjusters.

10. A method of treating the eye for irritation and dryness, comprising contacting said eye with an ophthalmic solution, consisting essentially of polyvinylpyrrolidone in an amount of about 0.100 by weight, a preservative in an effective amount, sodium borate/boric acid buffer, glycerin in an amount of about 0.200% by weight, and hydroxypropyl methylcellulose, in an amount of about 0.500% by weight of said solution, wherein said composition is an aqueous solution, having isotonic properties with respect to an eye and having, at 25° C., a viscosity of less than about 5 cps and a surface tension of less than about 40 dynes per centimeter.

11. The method of claim 10 wherein said solution contains BAK as a preservative in an amount of about 0.010% by weight.

12. The method of claim 10 wherein said solution contains a preservative selected from the group consisting of BAK, sorbic acid, chlorobutanol, disodium ethylenediamme tetracetate, polyquaternium-1 or acetamide.

* * * * *